(12) United States Patent
Huang et al.

(10) Patent No.: US 8,110,655 B2
(45) Date of Patent: Feb. 7, 2012

(54) METHOD TO PROMOTE HAIR GROWTH AND/OR DELAY OR TREAT HAIR LOSS BY ADMINISTERING A TGF-β ANTAGONIST OR INHIBITOR

(75) Inventors: Jung San Huang, St. Louis, MO (US); Shuan Shian Huang, St. Louis, MO (US)

(73) Assignees: Auxagen, Inc., St. Louis, MO (US); Saint Louis University, St. Louis, MO (US)

( * ) Notice: Subject to any disclaimer, the term of this patent is extended or adjusted under 35 U.S.C. 154(b) by 569 days.

(21) Appl. No.: 11/939,126

(22) Filed: Nov. 13, 2007

(65) Prior Publication Data

US 2008/0286229 A1   Nov. 20, 2008

Related U.S. Application Data

(60) Provisional application No. 60/858,592, filed on Nov. 13, 2006.

(51) Int. Cl.
*C07K 14/00* (2006.01)
*C07K 14/495* (2006.01)
(52) U.S. Cl. .................. 530/324; 514/21.3; 530/399
(58) Field of Classification Search .................. 530/324, 530/399; 514/21.3
See application file for complete search history.

(56) References Cited

U.S. PATENT DOCUMENTS

| | | | | |
|---|---|---|---|---|
| 5,118,791 | A | * | 6/1992 | Burnier et al. ............ 530/326 |
| 5,616,561 | A | * | 4/1997 | Barcellos-Hoff .......... 514/13 |
| 5,824,297 | A | | 10/1998 | Iwata et al. |
| 6,075,005 | A | * | 6/2000 | Lurie ....................... 514/2 |
| 6,500,920 | B1 | | 12/2002 | Haung |
| 6,838,076 | B2 | | 1/2005 | Patton et al. |
| 2006/0153794 | A1 | * | 7/2006 | Hibino et al. ............. 424/74 |
| 2006/0233708 | A1 | | 10/2006 | Huang |

OTHER PUBLICATIONS

Van Scott (Journal of Investigative Dermatology 29(3), 205-12, 1957.*
Chow (Nature 203, 847-848, 1964).*
Demetriou, Journal of Biological Chemistry 271, 12755, 1996.*
Huang et al., "Transforming Growth Factor Beta Peptide Antagonists and Their Conversion to Partial Agonists," J. Biol. Chem., 272(43): 27155-9 (1997).
Huang, Jung San, et al., Synthetic TFG-Beta Antagonist Accelerates Wound Healing and Reduces Scarring, The FASEB Journal, express article 10.1096/fj.02-0103fje. Published online Jun. 21, 2002.
Keita Inoue, M.D. et al., TGF-β2 is specifically expressed in human dermal papilla cells and modulates hair folliculogenesis, Journal of Cellular and Molecular Medicine, dated Oct. 16, 2008 (29 pages).

* cited by examiner

*Primary Examiner* — David Lukton

(57) ABSTRACT

The present invention provides methods for promoting hair growth and/or treating or preventing hair loss (alopecia) by contacting the cells with a TGF-β antagonist or inhibitor either alone or in combination with other alopecia-inhibiting compounds.

12 Claims, No Drawings

METHOD TO PROMOTE HAIR GROWTH AND/OR DELAY OR TREAT HAIR LOSS BY ADMINISTERING A TGF-β ANTAGONIST OR INHIBITOR

RELATED APPLICATIONS

This application claims the benefit of U.S. Provisional Application No. 60/858,592, filed on Nov. 13, 2006. The entire teachings of the above application are incorporated herein by reference.

GOVERNMENT SUPPORT

This invention was made with government support under grant number AR052578 awarded by National Institutes of Health. The government has certain rights in the invention.

BACKGROUND OF THE INVENTION

Alopecia (hair loss) is a common condition that results from diverse causes. For example, adrenergic alopecia (common baldness) is seen in the vast majority of adult males and is considered physiologic and part of the aging process. Besides the loss of hair, the length and diameter of each hair will be reduced in the adjacent areas even though the follicles remain intact.

Telogen effluvium is a transient, reversible, diffuse shedding of hair in which a high percentage of hair follicles enter the telogen phase prematurely as a result of physical or mental illness. Among the most important factors incriminated are childbirth, high fever, hemorrhage, sudden starvation, accidental or surgical trauma, severe emotional stress, and certain drugs.

Alopecia areata is an immunologic alopecia characterized by the abrupt onset of sharply defined areas of hair loss. In the most severe cases, the scalp will develop total hair loss (alopecia totalis) or the hair loss will involve the whole body surface (alopecia universalis). Most of the patients will run an unpredictable and relapsing course with multiple episodes of hair loss and regrowth. Only about 20 to 30 percent will have a single reversible episode. Regrowth of hair is common within several months, but in many instances is not complete, and relapses are common. Alopecia areata may be associated with autoimmune diseases such as vitiligo, pernicious anemia, collagen disease, and endocrinopathies.

Traumatic alopecia is induced by physical trauma, of which the two most important groups, from the therapeutic standpoint are trichotillomania and alopecia resulting from cosmetic procedures or improper hair care. Trichotillomania is a compulsive habit in which the individual repeatedly pulls or breaks off his or her own hair in a partially conscious state similar to thumb sucking or nail biting. Traumatic alopecia from cosmetic procedures is done consciously in ill-advised individuals and is almost exclusively seen among females. Sometimes this type of alopecia is associated with folliculitis induced by the occlusive effect of the oily cosmetics used in the procedure.

Anagen effluvium is a temporary alopecia caused by the inhibition of mitosis in the hair papilla by certain cytotoxic drugs, leading to constriction of the hair shaft or to complete failure of hair formation. In particular, alopecia frequently occurs in cancer patients who are treated with chemotherapeutic drugs such as cyclophosphamide (CY) and/or irradiation. Such agents damage hair follicles which contain mitotically active hair-producing cells. Such damage may cause abnormally slow growth of the hair or may lead to frank loss. While various attempts have been made to protect against alopecia or abnormal rates of hair growth during such treatments, there remains a need for an agent that prevents damage to hair follicles in a safe and effective manner.

Alopecia may also result from nutritional deficiencies and metabolic defects. Caloric deprivation must be very severe to produce hair loss. Increased shedding sometimes occurs after marked weight loss for obesity. Anemia, diabetes, hyper- and hypovitaminosis, and zinc deficiency may also lead to alopecia.

Treatments for androgenetic alopecia have been ineffective in inducing regrowth. The use of cyclic estrogen therapy in females with an estrogen-dominant contraceptive or topical estrogen has been advocated to reduce the rate of hair loss, but results are not impressive. The claim that topical testosterone induces the growth of terminal hairs in bald scalp of males has not been confirmed.

There have been some indications that minoxidil (Rogaine®, Upjohn), a potent vasodilator, has been effective in causing scalp hair regrowth in patients with androgenetic alopecia, but the results have been mixed. Thus, there remains a need in the art for methods of treating and preventing the various types of alopecia.

Transforming growth factor-β (TGF-β) is a family of structurally homologous dimeric proteins; three mammalian isoforms (TGF-$\beta_1$, TGF-$\beta_2$, TGF-$\beta_3$) share 70% sequence identity and exhibit distinct functions in vivo. All three TGF-β isoforms are potent growth inhibitors for most cell types, induce apoptosis in certain cell types and are physiologically important. TGF-β isoforms regulate multiple biological processes, including hair growth. TGF-β has been implicated in promoting the regression phase (catagen) of hair growth cycle by inducing cellular growth inhibition or apoptosis during anagen-catagen transition. Hair follicles are composed primarily of epithelial and dermal components.

The hair growth cycle is coordinated with the interactions of epithelial and dermal components. Dermal papilla cells (DPCs), which are androgen target cells, are believed to mediate androgenetic alopecia by androgen-induced secretion of TGF-β. The secreted TGF-β induces growth inhibition and/or apoptosis of hair follicle epithelial cells, resulting in loss of hair follicles and resultant alopecia. Increasing evidence also indicates that TGF-β is involved in the pathogenesis of alopecia caused by other factors. TGF-β therefore, appears to be the target for innovative treatment of alopecia. The present invention provides TGF-β peptantagonists and derivatives thereof that are effective in promoting hair growth.

SUMMARY OF THE INVENTION

The present invention provides methods for promoting hair growth and/or treating or preventing hair loss (alopecia) by contacting the cells with a TGF-β antagonist or inhibitor either alone or in combination with other alopecia-inhibiting compounds.

DESCRIPTION OF THE INVENTION

Unless otherwise indicated, the term "active agent" as used herein refers to the group of compounds comprising Transforming Growth Factor β (TGF-β) antagonists or inhibitors with specificities toward the type V TGF-β receptor and other TGF-β receptor types (type I, type II, and type III receptors) including peptides containing the W(or R)XXD motif (wherein X represents any amino acid) in the sequences and further including such peptides conjugated to carriers such as proteins or synthetic polymers, such as PEG, for example.

"Other compounds, for treating or preventing alopecia" include but are not limited to minoxidil, procyanidin B-3, finasteride, keratinocyte growth factor (KGF), fibroblast growth factor (FGF), epidermal growth factor (EGF), butyric acid and its derivatives, ammonium trichloro(dioxy ethylene-0,0') tellurate (AS101), interleukin 1, prostaglandin E2, cyclosporine A, corticosteroids such as dexamethasone, Imuvert™ (immunomodulatory preparation of membrane and ribosomes from Serratia marcescens), cholesterol and calcitriol (1,25 dihydroxyvitamin D).

As used herein, "alopecia" refers to hair loss associated with conditions including, but not limited to, adrenergic alopecia, telogen effluvium, alopecia areata, traumatic alopecia, anagen effluvium, and hair loss associated with nutritional deficiencies, metabolic defects, marked weight loss, diabetes, hyper- and hypovitaminosis, and zinc deficiency, alopecia vulgaris, alopecia pustulosa, alopecia erythrodermica, alopecia arthropathica, paraalopecia, palmoplantar pustulosis, all forms of ichthyoses, e.g. ichthyosis vulgaris and congenital ichthyoses, keratodermias of all types, e.g., palmoplantar keratodermia, other genodermatoses with pathological cornification disorders, e.g. Darier's disease, further lichen ruber planus and pityriasis rubra pilaris.

By "treating or preventing alopecia" is meant the ability to cure, reduce or prevent one or more clinical symptoms of alopecia, including, but not limited to, hair loss, cornification, scaling, uneven thickness, persistent itch, inflammation, and rapid epithelial cell turnover in the skin. Treating alopecia also includes the promotion of hair growth at the site of the hair loss. The methods of the invention also encompass promotion or stimulation of hair growth in general (e.g. to thicken naturally thin hair). The inventors have previously discovered that three chemically synthesized peptides $\beta_1^{25}$ (41-65) (SEQ ID NO: 4), $\beta_2^{25}$ (41-65) (SEQ ID NO: 5), and $\beta_3^{25}$ (41-65) (SEQ ID NO: 6) collectively referred to herein as "peptantagonists" or "antagonists", whose amino acid sequences were derived from and correspond to the 41st to 65th amino acid residues of TGF-$\beta_1$ (SEQ ID NO: 1), TGF-$\beta_2$ (SEQ ID NO: 2), and TGF-$\beta_3$ (SEQ ID NO: 3) respectively, inhibit the binding of radiolabeled TGF-$\beta_1$, TGF-$\beta_2$, and TGF-$\beta_3$ to TGF-$\beta$ receptors in mink lung epithelial cells which are a standard model system for investigating TGF-$\beta$ action and other cell types in humans and animals (i.e. cellular receptors). It was also discovered that at least four consecutive amino acids comprising W(or R)XXD (wherein X is any amino acid) motif in the sequences, determines their potencies and that they block TGF-$\beta$-induced growth inhibition and TGF-$\beta$-induced expression of PAI-1 in mink lung epithelial cells and other cell types (U.S. Pat. No. 6,500,920 issued Dec. 31, 2002). As was previously disclosed by the inventors, such peptides are effective in inhibiting, ameliorating or reversing the effects of TGF-$\beta$ in biological systems including but not limited to reducing scarring wounds, to prevent lung injury in adult respiratory distress syndrome (ARDS), and injuries of other tissues caused by pharmacological agents (e.g. bladder injury caused by cyclophosphamide).

The inventors have also discovered that derivatives of the peptide antagonists of the invention are also potent inhibitors of TGF-$\beta$. These derivatives of TGF-$\beta_3^{25}$ peptantagonists $\beta_1^{25}$ (41-65) (SEQ ID NO: 4), $\beta_2^{25}$ (41-65) (SEQ ID NO: 5), and $\beta_3^{25}$ (41-65) (SEQ ID NO: 6) are collectively referred to herein interchangeably as "TGF-$\beta$ peptantagonist derivatives", "TGF-$\beta$ antagonist derivatives" or "TGF-$\beta$ peptide derivatives".

However, prior to the present invention, there was no expectation by one of skill in the art that the TGF-$\beta$-derived peptides or derivatives thereof are useful in methods to promote hair growth and/or to treat or prevent alopecia.

Preferred active agents in accordance with the present invention comprise TGF-$\beta$ peptantagonists, $\beta_1^{25}$ (41-65) (SEQ ID NO: 4), $\beta_2^{25}$ (41-65) (SEQ ID NO: 5, and $\beta_3^{25}$ (41-65) (SEQ ID NO: 6), whose amino acid sequences were derived from and correspond to the 41st to 65th amino acid residues of TGF-$\beta_1$ (SEQ ID NO: 1), TGF-$\beta_2$ (SEQ ID NO: 2), and TGF-$\beta_3$ (SEQ ID NO: 3). In addition to these peptides, various nonpeptidic agents (e.g., peptidomimetics) having the requisite TGF-$\beta$ antagonist activity are further contemplated for use in accordance with the present invention.

In one preferred embodiment, the invention provides TGF-$\beta$ peptantagonist derivatives which are the result of the conjugation of polyethylene glycol (PEG) to $\beta_1^{25}$ (41-65) (SEQ ID NO: 4), $\beta_2^{25}$ (41-65) "(SEQ ID NO: 5), and $\beta_3^{25}$ (41-65)" (SEQ ID NO: 6), referred to herein as "PEG-$\beta_1^{25}$", "PEG-$\beta_2^{25}$" and "PEG-$\beta_3^{25}$", respectively, and collectively referred to herein as "PEG-$\beta^{25}$ peptantagonists". The conjugation of PEG to form peptides of the invention is referred to herein as "pegylation" and the peptides formed thereby are referred to herein as "pegylated". Pegylated (PEG-) TGF-$\beta$ peptantagonist derivatives can be generated in different molecular weight forms. The PEG group may be of any convenient molecular weight and may be linear or branched. The average molecular weight of the PEG will preferably range from about 2 kiloDalton ("K") to about 100 K, more preferably from about 5 K to about 50 K, more preferably from about 20 K to about 40 K, and most preferably from abut 20 K to about 30 K (the term "about" indicating that in preparations of PEG, some molecules will weigh more, some less, than the stated molecular weight). One skilled in the art will be able to select the desired polymer size based on such considerations as the desired dosage; circulation time; resistance to proteolysis; effects, if any, on biological activity; ease in handling; degree or lack of antigenicity; and other known effects of PEG on a therapeutic peptide.

The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group). The TGF-$\beta$ peptantagonist derivatives of the invention can also contain two PEG moieties that are covalently attached via a reactive group on each of the PEG moieties. Each PEG moiety preferably has a molecular weight of about 10 kilodaltons (10K) to about 60K. More preferably, each of the two PEG moieties has a molecular weight of about 20K to about 40K, and still more preferably between about 20K and about 40K. Still more preferably, each of the two PEG moieties has a molecular weight of about 20K. One skilled in the art will be able to select the desired polymer size based on such considerations as the desired dosage; circulation time; resistance to proteolysis; effects, if any, on biological activity; ease in handling; degree or lack of antigenicity; and other known effects of PEG on a therapeutic peptide.

In one preferred embodiment, the PEG-$\beta^{25}$ peptantagonists are pegylated at the N-terminal alpha-amino group and at the epsilon-amino group (e.g. the lysine residue) of the $\beta^{25}$ peptantagonists. In one embodiment $\beta_1^{25}$ (41-65) (SEQ ID NO: 8) is pegylated at the N-terminal alpha-amino group and at the epsilon-amino group to form PEG-$\beta_1^{25}$ as is indicated in bold in the following sequence:

NH2-ANFSLGPSPYIWSLDTQYSKVLALY-COOH. (SEQ ID NO: 8)

A useful strategy for the pegylation of synthetic peptides consists of combining, through forming a conjugate linkage in solution, a peptide and a PEG moiety, each bearing a special functionality that is mutually reactive toward the other. The peptides can be easily prepared with conventional solid phase synthesis as is known in the art and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), *The Proteins* (3rd ed.) 2: 105-253; and Erickson et al. (1976), The Proteins (3rd ed.) 2: 257-527. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The pegylated peptides can be easily purified by preparative HPLC and characterized by analytical HPLC, amino acid analysis and laser desorption mass spectrometry.

For a discussion of other strategies for the pegylation of peptides that would result in suitable TGF-β peptantagonist derivatives of the invention include those modifications that are described in U.S. Pat. Nos. 6,838,076 and 7,084,245, incorporated herein by reference.

The invention also includes TGF-β peptide derivatives and TGF-β peptantagonist derivatives comprising hydrophilic protein, peptide or organic polymer derivatizations. Suitable hydrophilic polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives. The TGF-β peptide derivatives and TGF-β peptantagonist derivatives of the invention may comprise modifications and derivatizations at random positions within the molecule, or at predetermined positions within the molecule and may include one, two, three or more attached chemical moieties.

The hydrophilic polymer or protein derivatizations may be of any molecular weight, and may be branched or unbranched. The size of the hydrophilic polymer or protein derivatizations may vary depending on the desired therapeutic profile (e.g., the duration of sustained release desired; the effects, if any, on biological activity; the ease in handling; the degree or lack of antigenicity and other known effects of the hydrophilic polymer derivatization to the TGF-β peptantagonist derivatives).

There are a number of attachment methods available to those skilled in the art. Preferred for therapeutic purposes is attachment at an amino group, such as attachment at the N-terminus or lysine group of the TGF-β peptantagonist. TGF-β peptantagonist derivatives chemically modified at the N-terminus may be accomplished by reductive alkylation, which exploits differential reactivity of different types of primary amino groups (lysine versus the N-terminal) available for derivatization in the TGF-β peptantagonist. Under the appropriate reaction conditions, substantially selective derivatization of the protein at the N-terminus with a carbonyl group containing polymer is achieved.

Examples of TGF-β peptantagonist derivatives comprising hydrophilic moieties attached at various positions within the molecule, include short, hydrophilic polymers such as polyglutamate, polyaspartate, polylysine or polyarginine attached to the N and/or C termini of a TGF-β peptantagonist derivative of the invention. TGF-β peptantagonist derivatives include the addition of 4 to 6 glutamate or aspartate residues at the N-termini or the C-termini of TGF-β peptantagonists. Preferred TGF-β peptantagonist derivatives include 6-glutamate, 6-aspartate, 4-lysine and 4-arginine derivatives.

Water soluble proteins such as albumin, (e.g. bovine serum albumin, human serum albumin), are also suitable for conjugation to peptides $\beta_1^{25}$ (41-65) (SEQ ID NO: 4), $\beta_2^{25}$ (41-65) (SEQ ID NO: 5), and $\beta_3^{25}$ (41-65) (SEQ ID NO: 6).

In another embodiment of the invention variants of peptantagonists $\beta_3^{25}$ (41-65) (SEQ ID NO: 4), $\beta_2^{25}$ (41-65) (SEQ ID NO: 5), and $\beta_3^{25}$ (41-65) (SEQ ID NO: 6), are provided in which cysteine-44 and cysteine-48 were replaced by serine residues. These C44S/C48S versions designated $\beta_1^{25}$ C44S/C48S (SEQ ID NO: 8), $\beta_2^{25}$ C44S/C48S (SEQ ID NO: 9), and $\beta_3^{25}$ C44S/C48S (SEQ ID NO: 10), had the same TGF-β antagonist activity. The C44S/C48S versions had better stability in solution during storage.

In another embodiment, the C44S/C48S variants designated $\beta_1^{25}$ C44S/C48S (SEQ ID NO: 8), $\beta_2^{25}$ C44S/C48S (SEQ ID NO: 9), and $\beta_3^{25}$ C44S/C48S (SEQ ID NO: 10), include further derivations as discussed above with regard to the conjugation of PEG (or other water soluble proteins) at various positions on the molecule (e.g. at the N-terminal alpha-amino group and/or at the epsilon-amino group (e.g. the lysine residue) and/or the attachment of hydrophilic moieties (e.g. 6-glutamate, 6-aspartate, 4-lysine and 4-arginine) at various positions in the molecule, and preferably at the N-terminus or C-terminus of the TGF-β peptantagonists. For example, in one embodiment a preferred peptide comprises $\beta_1^{25}$ C44S/C48S (SEQ ID NO: 8) that has been derivitized with 6 glutamate at the N-terminus and is designated herein as 6-E-$\beta_1^{25}$ C44S/C48S (SEQ ID NO: 7). Examples of other peptantagonist derivatives comprising hydrophilic moieties include but are not limited to: 6-E-$\beta_2^{25}$ C44S/C48S (SEQ ID NO: 11), and 6-E-$\beta_3^{25}$ C44S/C48S (SEQ ID NO: 12).

The polypeptides of the instant invention may be synthesized by any conventional method, including, but not limited to, those set forth U.S. Pat. No. 6,500,920 incorporated herein by reference. Briefly, the amino acid sequences of all TGF-β peptantagonists and TGF-β peptantagonist derivatives were derived from those of TGF-$\beta_1$ (SEQ ID NO: 1), TGF-$\beta_2$ (SEQ ID NO: 2), and TGF-$\beta_3$ (SEQ ID NO: 3). The peptides were synthesized using solid phase methods and purified using Sephadex G-25 column chromatography and HPLC. The purity of the synthesized peptides was verified by automated MALDY-TOF/TOF and MS/MS analyses.

In one aspect of the present invention, a method of treating or preventing alopecia by administering to a patient in need thereof an amount effective to treat or prevent alopecia of the TGF-β peptantagonists or TGF-β peptantagonist derivatives in accordance with the invention, is disclosed, either alone, combined, or in further combination with other compounds or treatments effective for treating or preventing alopecia.

In one preferred embodiment, the method is used to limit alopecia in a patient subjected to radiation or chemotherapy treatment and/or promote hair growth in such patient.

The active agents may be made up in a solid form (including granules or powders) or in a liquid form (e.g., solutions, suspensions, or emulsions), and may be subjected to conventional pharmaceutical operations such as sterilization and/or may contain conventional adjuvants, such as stabilizers, wetting agents, emulsifiers, preservatives, cosolvents, suspending agents, viscosity enhancing agents, ionic strength and osmolality adjustors and other excipients in addition to buffering agents. Suitable water soluble preservatives which may be employed in the drug delivery vehicle include sodium bisulfite, sodium thiosulfate, ascorbate, benzalkonium chloride, chlorobutanol, thimerosal, phenylmercuric borate, parabens, benzyl alcohol, phenylethanol or antioxidants such as Vitamin E and tocopherol and chelators such as EDTA and EGTA. These agents may be present, generally, in amounts of about 0.001% to about 5% by weight and, preferably, in the amount of about 0.01 to about 2% by weight.

For administration, the active agents are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose gel solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

For use in treating or preventing alopecia, the active agents may be administered by any suitable route, including local delivery, parentally, transdermally, intradermally or topically in dosage unit formulations containing conventional pharmaceutically acceptable carriers, adjuvants, and vehicles. The term parenteral as used herein includes, subcutaneous, intravenous, intramuscular, intrasternal, intratendinous, intraspinal, intracranial, intrathoracic, infusion techniques or intraperitoneally.

For topical administration, the active agents may be formulated as is known in the art for direct application to a target area. Conventional forms for this purpose include wound dressings, coated bandages or other polymer coverings, ointments, lotions, creams, pastes, jellies, sprays, shampoos, salves, transdermal patches, and aerosols. The percent by weight of the active agent of the invention present in a topical formulation will depend on various factors, but generally will be from 0.01% to 50% of the total weight of the formulation, and typically 1-10% by weight.

Liquid, emulsion or gel dosage forms for topical or intradermal administration may include pharmaceutically acceptable emulsions, solutions, suspensions, syrups and elixirs containing inert diluents commonly used in the art, such as water. Such compositions may also comprise adjuvants, such as wetting agents, emlusifying and gel agents and -dermal permeability enhancers, flavoring and perfuming agents.

The dosage and treatment regimen for treating or preventing alopecia with the active agents is based on a variety of factors, including the age, weight, sex, medical condition of the individual, the severity of the condition, the route of administration, and the particular compound employed. Thus, the dosage regimen may vary widely, but can be on the order of between 0.01 mg/cm$^2$ and 10 mg/cm$^2$ of the active agents per cm$^2$ of body surface are useful for topical methods as disclosed herein, preferably between about 0.1 mg/cm$^2$ and 5 mg/cm$^2$, more preferably between about 0.1 mg/cm$^2$ and 2.5 mg/cm$^2$, and most preferably between about 0.1 mg/cm$^2$ and 1 mg/cm$^2$ For example, treatment of alopecia using the composition may be accomplished by subcutaneous or topical application of the composition to the affected areas one or more times per day for as long as is needed.

It may also be envisaged that the composition comprising at least one TGF-β antagonist is in liposomal form. Thus, the antagonist encapsulated in the liposomes can be delivered selectively to the hair follicle. Such composition may be applied to alopecic areas of an individual's scalp and hair, and is optionally left in contact for several hours and a rinsing operation is optionally carried out. It is possible, for example, to apply the composition containing the active agent in the evening, to keep it in contact throughout the night and optionally to shampoo the hair in the morning. These applications can be repeated daily for one or more months depending on the individual. The treatment process has the characteristics of a cosmetic process insofar as it allows the aesthetic appeal of the hair to be enhanced by making it more vigorous and improving its appearance.

The pharmaceutical compositions of the invention may be formulated as to provide rapid, sustained or delayed release of the active ingredients after administration to the patient by employing procedures well known in the art. The formulations may also contain substances that diminish proteolytic degradation and promote absorption such as, for example, surface active agents.

In a further aspect, the present invention provides kits for treating or preventing alopecia, wherein the kits comprise an effective amount of the active agents of the invention to treat or prevent alopecia, and instructions for using the amount effective of active agent to treat or prevent alopecia.

In a preferred embodiment, the kits also contain an effective amount to treat or prevent alopecia of one or more other compounds, including but not limited to minoxidil, procyanidin B-3, finasteride, phosphatidic acid, keratinocyte growth factor (KGF), fibroblast growth factor (FGF), epidermal growth factor (EGF), zinc ions butyric acid and its derivatives, ammonium trichloro(dioxy ethylene-0,0') tellurate (AS101), interleukin 1, prostaglandin E2, cyclosporine A, corticosteroids such as dexamethasone, Imuvert™ (immunomodulatory preparation of membrane and ribosomes from *Serratia marcescens*), cholesterol and calcitriol (1,25 dihydroxyvitamin D). Effective dosages of the active agents of the invention to treat or prevent alopecia are between about 0.1 mg/cm$^2$ and 1 mg/cm$^2$, as discussed above.

In another aspect of the invention, pharmaceutical compositions are provided that comprise an amount effective to treat or prevent alopecia of one or more of the active agents of the invention in combination with an amount effective to treat or prevent alopecia of minoxidil, procyanidin B-3, finasteride, phosphatidic acid keratinocyte growth factor (KGF), fibroblast growth factor (FGF), epidermal growth factor (EGF), butyric acid and its derivatives, ammonium trichloro(dioxy ethylene-0,0') tellurate (AS101), interleukin 1, prostaglandin E2, cyclosporine A, corticosteroids such as dexamethasone, Imuvert™ (immunomodulatory preparation of membrane and ribosomes from *Serratia marcescens*), cholesterol and calcitriol (1,25 dihydroxyvitamin D).

The invention is further illustrated by the following non limiting examples.

Example 1

Hair Growth Studies in Full-Thickness Porcine Burn Wounds

Preparation of 6-E (Glutamate)-$\beta^{25}$ Peptantagonists:

TGF-β peptantagonists with amino acid sequences corresponding to residues 41-65 of TGF-$\beta_1$ (SEQ ID NO: 8) and TGF-$\beta_2$ (SEQ ID NO: 9), and TGF-β peptantagonist 6-$\beta_1^{25}$ (SEQ ID NO: 7), which have additional 6 glutamate residues at the N-termini were synthesized and purified as described previously. Sterile IntraSite gel was obtained from Smith and Nephew Medical, Ltd. (UK) and mixed with TGF-β peptantagonists in phosphate-buffered saline at a ratio of 3:1 (v/v).

Animals:

Female pigs (Yorkshire strain, house inbred and specific pathogen-free) weighing 20-25 kg were used in the experiments. The pigs were housed in individual rooms. They were fed standard laboratory chow and water ad libitum. All study protocols were reviewed and approved by the respective institutional animal care committees.

Preparation of IntraSite Gel Containing TGF-β Peptantagonist $6-\beta_1^{25}$:

One milliliter of sterile 3 mM each of TGF-β peptantagonist $6-E-\beta_1^{25}$ (SEQ ID NO: 7), in phosphate-buffered saline (PBS) or 1 ml of sterile PBS (vehicle) was vigorously mixed with 3 ml of IntraSite gel using two 10 ml syringes connected with a three-way connector. The IntraSite gel containing $6-E-\beta_1^{25}$ and IntraSite gel containing buffer (vehicle) were stable for at least 2 months. The biological activity of TGF-β peptantagonist in IntraSite gel containing $6-E-\beta_1^{25}$ was analyzed by determining its activity to block $^{125}$I-TGF-β binding to TGF-β receptors in mink lung epithelial cells. Two concentrations of TGF-β peptantagonist (0.15 and 0.6 mM) were found to be effective in promoting hair growth.

Hair Growth in Full-Thickness Pig Skin Burn Wound Model:

Four pigs weighing 20-25 kg were anesthetized by intramuscular injection of ketamine (5 mg/kg), strenil (cazaporonum) (20 mg/kg), and atropine (5 mg/kg). Six uniform burn wounds (110° C., 30 s) were then made symmetrically on the back of each pig using a modified soldering iron with a flat contact area of 20 cm². The burn injury was equivalent to a full-thickness burn injury in humans and uniformly caused coagulation and necrosis of dermis, and complete loss of hair in the burn lesion. After wounding, IntraSite gels containing $6-E-\beta_1^{25}$ and buffer vehicle (as control) were applied to the pig burn wounds. All wounds were dressed with paraffin gauze. TGF-β peptantagonist gel or control gel was applied to the wounds every 2 days for the first 10 days and twice a week for the next 30 days. All wounds were cleaned and measured before each application of the IntraSite gel.

Measurement of Hair Growth:

Hair growth was assessed by measuring hair number and hair length in the burn lesion and around the lesion area. Hair growth was monitored every 2 days for the first 10 days and twice a week for 30 more days. Hair growth expressed as a percent of the original wound size was calculated.

Results

The pig model is commonly used in skin injury (e.g., burn) experiments because porcine skin is anatomically very similar to human skin. It was used to determine the ability of $6-E-\beta_1^{25}$ peptantagonist to rescue or restore hair follicles and to promote hair growth in a standardized burn injury. Four pigs weighing 20-25 kg were anesthetized by intramuscular injection of ketamine (5 mg/kg). A soldering iron with a flat contact area of ~20 cm² was used to generate full-thickness burn wounds (110° C., 30 s) at standard sites on the skin of the back. Six thermal burns (three on each side) were created on each pig. After wounding, two lesions were treated with a thin layer of IntraSite gel containing $6-E-\beta_1^{25}$ (SEQ ID NO: 7) (0.15 and 0.6 mM); two received gel alone and two received no topical applications. All wounds were then bandaged and protected from potential contact irritation with a fixed frame. $6-E-\beta_1^{25}$ (SEQ ID NO: 7) and vehicle gels were applied every 2 days for the first 10 days and twice a week for the next 30 days, at which time hair growth was measured and photographed. Each animal served as its own control. The burn wounds at postburn day 0 showed homogeneous necrosis (the white color region). On postburn day 30, wounds treated with $6-E-\beta_1^{25}$ exhibited re-epithelialization and hair growth. The $6-E-\beta_1^{25}$ peptantagonist appeared to promote hair growth in a dose-dependent manner. At 0.15 and 0.6 mM, $6-E-\beta_1^{25}$ (SEQ ID NO: 7) promoted hair growth of 5-10 and 30-40% of the original pre-burn area, respectively. Interestingly, at these dosages, $6-E-\beta_1^{25}$ also promoted hair growth in the area surrounding the burn wound. By contrast, wounds treated with vehicle only (control) exhibited re-epithelialization but did not exhibit any hair growth at postburn day 30 and even in the experimental time period (40 days). Furthermore, the control wound did not show accelerated hair growth in the area surrounding the wound when compared with those treated with $6-E-\beta_1^{25}$ (SEQ ID NO: 7). This result indicates that $6-E-\beta_1^{25}$ (SEQ ID NO: 7) is capable of restoring or rescuing hair follicles and promoting hair growth.

Example 2

Hair Growth Studies in Partial-Thickness Porcine Burn Wounds

Study Protocol and Interventions:

Animals were sedated with Talazine® (Tiletamine and Zolazepam, Fort Dodge Lab, Fort Dodge, Iowa) 5 mg/kg IM. The pigs were then intubated endotracheally and maintained under a surgical plane of anesthesia with isoflurane 0.5-2.5% in room air. The flank and back hair was clipped with hair clippers and the skin was scrubbed with a povidine iodine solution.

Standardized partial thickness burns were created on the animals' backs and flanks by applying a 2.5 cm by 2.5 cm, 150 gram aluminum bar preheated in hot water to 80° C. The heated bar was wiped dry just prior to application to prevent water droplets from creating a steam burn on the skin. The bar was then placed at a vertical position perpendicular to the skin's surface and applied for a period of 20 seconds with all pressure supplied by gravity. This burn model results in damage to the upper 30-50% of the dermis and has been shown to be highly reproducible. In order to simulate burn blister debridement and enhance the absorption of the topical agents, the necrotic epidermis was gently removed by rubbing the burn with dry gauze. Removal of the necrotic epidermis results in delayed reepithelialization, and increased scar formation[17]. Twenty burns were inflicted on each of 2 pigs (evenly distributed between both side of the pigs), for a total of 40 burns.

PEG-$\beta_1^{25}$ Peptantagonist:

The agent used in the studies is PEG-$\beta_1^{25}$ (SEQ ID NO: 8) This particular peptide was chosen after screening seven pentacosapeptides whose amino acids overlap and cover most of the human TGF-$\beta_1$ molecule, the monomer of which has 112 amino acid residues. The antagonist activities of the chosen peptide completely inhibited the binding of labeled TGF-$\beta_1$ to its receptor in mink lung epithelial cells. The other six peptides did not show any effect on labeled TGF-$\beta_1$ binding to its receptor. Furthermore, the chosen peptide was also shown to block the cellular responses to TGF-$\beta_1$ such as DNA synthesis and transcriptional activation of PAI-1. Polyethylene glycol propionic acid N-hydroxysuccimide ester (M.W. 5000, 20000 and 30000) were obtained from Necktar. PEG-TGF-β peptantagonists PEG-$\beta_{1-3}^{25}$ were prepared by reacting polyethylene glycol propionic acid N-hydroxysuccimide ester with TGF-β peptantagonist $\beta_{1-3}^{25}$ according to the protocol provided by the manufactural company. TGF-β peptantagonist PEG-$\beta_1^{25}$ in PBS was mixed with Sterile IntraSite gel from Smith and Nephew Medical, Ltd. (UK) at a ratio of 1:3 (v/v).

Hair Growth in Partial-Thickness Pig Skin Burn Wound Model:

The pigs were randomized to treatment with topical PEG-$\beta_1^{25}$ peptantagonist (SEQ ID NO: 8) or its vehicle (carboxymethylcellulose, IntraSite Gel, Smith and Nephew, Largo, Fla.) immediately after injury and at days 3, 5, 7, 10, 14, 18, 21, and 25. A thin layer of the topical treatment was applied with a sterile metal spatula. Group randomization order was determined by drawing unlabeled forms from an opaque container. After applying the topical therapy, the burns were covered with dry non-adherent gauze (Telfa®, Kendall Company, Mansfield, Mass.). The burned areas were then covered with a gauze bandage roll (Conform®), Kendall Healthcare Products Company, Mansfield, Mass.) and an adhesive elastic bandage (Elastoplast®, Beiersdorf-Jobst, Inc., Rutherford College, N.C.). The adhesive dressing was secured to the skin at a distance from the burns with skin staples. Animals were observed frequently for signs of pain or discomfort and treated with IM buprenorphine 0.01 mg/kg as needed.

Dressing changes were performed with each application of the topical agents. At each dressing change all gauze dressings were removed and the wounds were observed and the study agent was reapplied. All burns were then re-covered with non-adherent gauze and elastic wrap as previously described. Full thickness 4-mm punch biopsies (Miltex Instrument Company Inc., Lake Success, N.Y.) were taken after 7, 10, and 14 days for blinded histopathological evaluation by a board-certified dermatopathologist masked to treatment assignment. The entire wound was excised at 28 days and submitted for histological evaluation. Digital photos were taken prior to biopsy to determine the presence of wound contraction defined as an hourglass like shape. Histopathological studies were done on formalin-fixed, alcohol-dehydrated, xylene-cleared, paraffin-embedded, hematoxylin and eosin stained 5 μm sections using conventional microscopy.

Outcomes:

The primary outcome was the percent of wounds healing with wound contraction. Secondary outcomes were percent reepithelialization, percent wound infection, and the percent of wounds with scars extending through the entire thickness of the dermis.

Wound contraction was considered present if the scar had an hourglass configuration. The percent reepithelialization was calculated by measuring the length of neoepidermis in cross section and dividing it by the specimen's diameter multiplied by 100 (inter-observer agreement, r=0.99) While there is considerable debate regarding the exact definition of wound infection, wounds were considered infected in the presence of erythema, warmth and/or purulence. Another outcome was the percentage of wounds with a deep full-thickness scar extending through the entire depth of the dermis. A scar is the end result of wound healing due to dermal damage or loss. It is characterized histopathologically by poorly organized thin bundles of collagen that are observed under polarized light. This measurement has excellent intra-observer reliability (K=0.93).

Data Analysis:

Data analysis was performed using SPSS 14.0 for Windows (SPSS, Inc., Chicago, Ill.) software. Categorical variables (wound contraction, full thickness scar) are expressed as the percent frequency of occurrence, and the study groups were compared with $\chi^2$ tests. Continuous variables (percent reepithelialization) were expressed as means with 95% confidence intervals and compared across groups using a t-test. The level of significance was preset at a P value of 0.05. A sample size of 20 burns in each group provided a power of 80% to detect a 25-percentage point difference in the percent of contracted wounds.

Results

Twenty burns were treated with a PEG-$\beta_1^{25}$ peptantagonist (SEQ ID NO: 8) and 20 burns with control vehicle. There were no wound infections in any of the study groups. The mean percent wound reepithelialization was higher at 7, 10, and 14 days in wound treated with the TGF-B antagonists, although the differences were not significant (Table 1).

TABLE 1

Partial-thicknness porcine Burn Wound Outcomes

| | PEG-$\beta_1^{25}$ peptantagonist | Control Vehicle | Mean Difference (95% CI) |
|---|---|---|---|
| Wound infections, No. (%) | 0 | 0 | |
| Percent wound reepithelialization, day 7 | 14.2 (28.8) | 6.2 (20.9) | 7.9 (−8.2-24.1) |
| Percent wound reepithelialization, day 10 | 46.3 (44.4) | 25.3 (39.9) | 20.9 (−6.1-48.0) |
| Percent wound reepithelialization, day 14 | 91.9 (25.7) | 72.4 (41.3) | 19.5 (−2.5-41.5) |
| No. (%) wounds completed reepithelialized, day 14 | 18 (90) | 9 (45) | P = 0.006 |
| No. (%) contracted wounds, day 28 | 7 (35%) | 13 (65%) | P = 0.025 |
| No. (%) deep scars, day 28 | 2 (10%) | 12 (60%) | P = 0.002 |

The percentage of wounds that were completely reepithelialized at 14 days after injury was significantly higher in burns treated with the PEG-$\beta_1^{25}$ than controls (90% vs. 45%, P=0.002). It is important to note that wounds treated with PEG-$\beta_1^{25}$ exhibited hair growth whereas wounds treated with vehicle only did not show any hair growth. The percentage of contracted wounds (35% vs. 65%, P=0.02) and full thickness scars (10% vs. 60%, P=0.002) at 28 days was also reduced in the PEG-$\beta_1^{25}$-treated groups. These results indicate that PEG-TGF-$\beta_1$ peptantagonist enhances wound healing and reduces scarring and suggest that PEG-$\beta_1^{25}$ restores and rescues hair follicles and promotes hair growth in partial-thickness pig skin burn wounds.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method to promote or stimulate hair growth and/or delay or treat hair loss in a subject, said method comprising administering an effective amount of at least one peptide TGF-β receptor antagonist to promote or stimulate hair growth and/or delay or treat hair loss to an individual in need thereof, wherein said peptide TGF-β receptor antagonist binds to a type I, type II, type III and/or type V TGF-β receptor and is capable of inhibiting binding of TGF-β to the receptor.

2. The method of claim 1 wherein the peptide TGF-β receptor antagonist comprises an amino acid sequence having at least four contiguous amino acids comprising W (or R)XXD wherein X is any amino acid.

3. The method of claim 2 wherein the amino acid sequence comprises at least 10 amino acids.

4. The method of claim 1 wherein the peptide TGF-β receptor antagonist has an amino acid sequence selected from: $\beta_1^{25}$ (41-65) (SEQ ID NO: 4), $\beta_2^{25}$ (41-65) (SEQ ID NO: 5), $\beta_3^{25}$ (41-65) (SEQ ID NO: 6), $\beta_1^{25}$ C44S/C48S (SEQ ID NO: 8), $\beta_2^{25}$ C44S/C48S (SEQ ID NO: 9), and $\beta_3^{25}$ C44S/C48S (SEQ ID NO: 10).

5. The method of claim 4 for treating alopecia.

6. The method of claim 5 wherein the alopecia is associated with a disorder selected from the group consisting of adrenergic alopecia, telogen effluvium, alopecia areata, traumatic alopecia, anagen effluvium, nutritional deficiencies, metabolic defects, marked weight loss, diabetes, hypervitaminosis, hypovitaminosis, zinc deficiency, alopecia vulgaris, alopecia pustulosa, alopecia erythrodermica, alopecia arthropathica, para-alopecia, palmoplantar pustulosis, ichthyoses, keratodermias, and genodermatoses with pathological cornification disorders.

7. The method of claim 5 further comprising the step of administering a therapeutically effective amount of another compound for treating alopecia, selected from the group consisting of minoxidil, procyanidin B-3, finasteride, phosphatidic acid, keratinocyte growth factor, fibroblast growth factor, epidermal growth factor, butyric acid and its derivatives, ammonium trichloro(dioxy ethylene-0,0') tellurate, interleukin 1, prostaglandin E2, cyclosporine A, corticosteroids, cholesterol and calcitriol.

8. The method of claim 4 wherein the peptide TGF-β receptor antagonist is a peptide TGF-β receptor antagonist derivative comprising at least one short, hydrophilic polymer attached to the N and/or C terminus of a peptide TGF-β receptor antagonist.

9. The method of claim 8 wherein the short, hydrophilic polymer is 6-glutamate, 6-aspartate, 4-lysine or 4-arginine residues.

10. The method of claim 9 wherein the peptide TGF-β receptor antagonist derivative is: 6-E-$\beta_1^{25}$ C44S/C48S (SEQ ID NO: 7), 6-E-$\beta_2^{25}$ C44S/C48S (SEQ ID NO: 11), or 6-E-$\beta_3^{25}$ C44S/C48S (SEQ ID NO: 12).

11. The method of claim 4 wherein the peptide TGF-β receptor antagonist is a pegylated peptide TGF-3 receptor antagonist derivative.

12. The method of claim 11 wherein the pegylated peptide TGF-β receptor antagonist derivative is pegylated at the N-terminal alpha-amino group, at the epsilon-amino group or at both the N-terminal alpha-amino group and the epsilon-amino group.

* * * * *

SEQUENCE LISTING

<160> NUMBER OF SEQ ID NOS: 12

<210> SEQ ID NO 1
<211> LENGTH: 112
<212> TYPE: PRT
<213> ORGANISM: Homo Sapiens

<400> SEQUENCE: 1

```
Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
 65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 2
<211> LENGTH: 112
<212> TYPE: PRT
<213> ORGANISM: Homo Sapiens

<400> SEQUENCE: 2

```
Ala Leu Asp Ala Ala Tyr Cys Phe Arg Asn Val Gln Asp Asn Cys Cys
 1               5                  10                  15

Leu Arg Pro Leu Tyr Ile Asp Phe Lys Arg Asp Leu Gly Trp Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
 65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 3
<211> LENGTH: 112
<212> TYPE: PRT
<213> ORGANISM: Homo Sapiens

<400> SEQUENCE: 3

```
Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Trp Lys Trp
                20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
```

```
                50                  55                  60
Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
                100                 105                 110

<210> SEQ ID NO 4
<211> LENGTH: 25
<212> TYPE: PRT
<213> ORGANISM: Homo Sapiens

<400> SEQUENCE: 4

Ala Asn Phe Cys Leu Gly Pro Cys Pro Tyr Ile Trp Ser Leu Asp Thr
 1               5                   10                  15

Gln Tyr Ser Lys Val Leu Ala Leu Tyr
                 20                  25

<210> SEQ ID NO 5
<211> LENGTH: 25
<212> TYPE: PRT
<213> ORGANISM: Homo Sapiens

<400> SEQUENCE: 5

Ala Asn Phe Cys Ala Gly Ala Cys Pro Tyr Leu Trp Ser Ser Asp Thr
 1               5                   10                  15

Gln His Ser Arg Val Leu Ser Leu Tyr
                 20                  25

<210> SEQ ID NO 6
<211> LENGTH: 25
<212> TYPE: PRT
<213> ORGANISM: Homo Sapiens

<400> SEQUENCE: 6

Ala Asn Phe Cys Ser Gly Pro Cys Pro Tyr Leu Arg Ser Ala Asp Thr
 1               5                   10                  15

Thr His Ser Thr Val Leu Gly Leu Tyr
                 20                  25

<210> SEQ ID NO 7
<211> LENGTH: 31
<212> TYPE: PRT
<213> ORGANISM: Homo Sapiens

<400> SEQUENCE: 7

Glu Glu Glu Glu Glu Ala Asn Phe Ser Leu Gly Pro Ser Pro Tyr
 1               5                   10                  15

Ile Trp Ser Leu Asp Thr Gln Tyr Ser Lys Val Leu Ala Leu Tyr
                 20                  25                  30

<210> SEQ ID NO 8
<211> LENGTH: 25
<212> TYPE: PRT
<213> ORGANISM: Homo Sapiens

<400> SEQUENCE: 8

Ala Asn Phe Ser Leu Gly Pro Ser Pro Tyr Ile Trp Ser Leu Asp Thr
 1               5                   10                  15

Gln Tyr Ser Lys Val Leu Ala Leu Tyr
                 20                  25
```

```
<210> SEQ ID NO 9
<211> LENGTH: 25
<212> TYPE: PRT
<213> ORGANISM: Homo Sapiens

<400> SEQUENCE: 9

Ala Asn Phe Ser Ala Gly Ala Ser Pro Tyr Leu Trp Ser Ser Asp Thr
 1               5                  10                  15

Gln His Ser Arg Val Leu Ser Leu Tyr
            20                  25

<210> SEQ ID NO 10
<211> LENGTH: 25
<212> TYPE: PRT
<213> ORGANISM: Homo Sapiens

<400> SEQUENCE: 10

Ala Asn Phe Ser Ser Gly Pro Ser Pro Tyr Leu Arg Ser Ala Asp Thr
 1               5                  10                  15

Thr His Ser Thr Val Leu Gly Leu Tyr
            20                  25

<210> SEQ ID NO 11
<211> LENGTH: 31
<212> TYPE: PRT
<213> ORGANISM: Homo Sapiens

<400> SEQUENCE: 11

Glu Glu Glu Glu Glu Glu Ala Asn Phe Ser Ala Gly Ala Ser Pro Tyr
 1               5                  10                  15

Leu Trp Ser Ser Asp Thr Gln His Ser Arg Val Leu Ser Leu Tyr
            20                  25                  30

<210> SEQ ID NO 12
<211> LENGTH: 31
<212> TYPE: PRT
<213> ORGANISM: Homo Sapiens

<400> SEQUENCE: 12

Glu Glu Glu Glu Glu Glu Ala Asn Phe Ser Ser Gly Pro Ser Pro Tyr
 1               5                  10                  15

Leu Arg Ser Ala Asp Thr Thr His Ser Thr Val Leu Gly Leu Tyr
            20                  25                  30
```